(12) United States Patent
Rudakov et al.

(10) Patent No.: US 6,451,050 B1
(45) Date of Patent: Sep. 17, 2002

(54) STENT GRAFT AND METHOD

(75) Inventors: Leon V. Rudakov, Belmont; Michi E. Garrison, Half Moon Bay, both of CA (US)

(73) Assignee: CardioVasc, Inc., Menlo Park, CA (US)

( * ) Notice: Subject to any disclaimer, the term of this patent is extended or adjusted under 35 U.S.C. 154(b) by 0 days.

(21) Appl. No.: 09/560,201

(22) Filed: Apr. 28, 2000

(51) Int. Cl.⁷ .................................................. A61F 2/06
(52) U.S. Cl. ...................................... 623/1.15; 623/1.42
(58) Field of Search ................................ 623/1.1–1.23, 623/1.32, 1.34, 1.36, 1.42, 1.43, 1.44, 1.46

(56) References Cited

U.S. PATENT DOCUMENTS

| | | | |
|---|---|---|---|
| 4,656,083 A | 4/1987 | Hoffman et al. | |
| 5,123,917 A | * 6/1992 | Lee | 623/1.13 |
| 5,217,492 A | 6/1993 | Guire et al. | |
| 5,282,824 A | * 2/1994 | Gianturco | 606/191 |
| 5,405,377 A | * 4/1995 | Cragg | 606/191 |
| 5,507,767 A | * 4/1996 | Maeda et al. | 606/198 |
| 5,591,140 A | 1/1997 | Narayanan et al. | |
| 5,609,629 A | * 3/1997 | Fearnot et al. | 604/265 |
| 5,643,580 A | 7/1997 | Subramaniam | |
| 5,653,747 A | 8/1997 | Dereume | |
| 5,667,523 A | 9/1997 | Bynon et al. | |
| 5,674,241 A | 10/1997 | Bley et al. | |
| 5,697,971 A | 12/1997 | Fischell et al. | |
| 5,843,117 A | 12/1998 | Alt et al. | |
| 5,866,113 A | 2/1999 | Hendriks et al. | |
| 5,911,754 A | 6/1999 | Kanesaka et al. | |
| 5,972,027 A | * 10/1999 | Johnson | 424/422 |
| 6,010,530 A | * 1/2000 | Goicoechea | 623/1 |
| 6,019,789 A | 2/2000 | Dinh et al. | |
| 6,022,374 A | 2/2000 | Imran | |
| 6,027,525 A | * 2/2000 | Suh et al. | 623/1 |
| 6,066,167 A | 5/2000 | Lau et al. | |
| 6,106,548 A | 8/2000 | Roubin et al. | |
| 6,110,198 A | * 8/2000 | Fogarty et al. | 623/1.12 |
| 6,156,063 A | * 12/2000 | Douglas | 623/1.11 |
| 6,165,210 A | * 12/2000 | Lau et al. | 623/1.12 |
| 6,206,915 B1 | * 3/2001 | Fagan et al. | 623/1.15 |
| 6,254,632 B1 | * 7/2001 | Wu et al. | 623/1.15 |
| 6,270,524 B1 | * 8/2001 | Kim | 606/194 |
| 6,273,908 B1 | * 8/2001 | Ndondo-Lay | 606/194 |
| 6,273,913 B1 | * 8/2001 | Wright et al. | 623/1.39 |
| 6,312,458 B1 | * 11/2001 | Golds | 623/1.13 |
| 6,322,585 B1 | * 11/2001 | Khosravi et al. | 623/1.11 |
| 6,355,055 B1 | * 3/2002 | Waksman et al. | 600/36 |

* cited by examiner

*Primary Examiner*—Michael J. Milano
*Assistant Examiner*—Tan-Uyen T. Ho
(74) *Attorney, Agent, or Firm*—Perkins Coie LLP; Peter J. Dehlinger; Larry W. Thrower

(57) ABSTRACT

A stent graft for implantation in a vessel in a human body comprising inner and outer concentric coaxial tubular sleeves formed of a flexible material compatible for use in the human body and each having first and second ends. A plurality of separate expandable metallic rings disposed axially within and between the inner and outer sleeves. Bands of a flexible material compatible with the flexible material utilized for the inner and outer sleeves disposed between the rings and within and between the inner and outer sleeves.

20 Claims, 2 Drawing Sheets

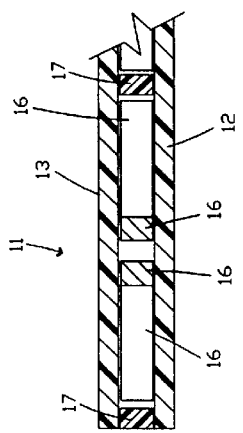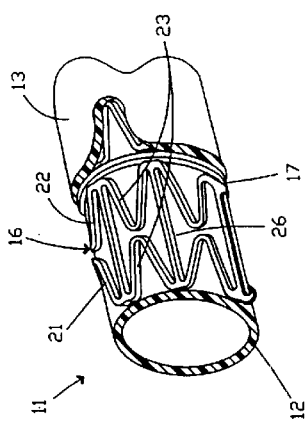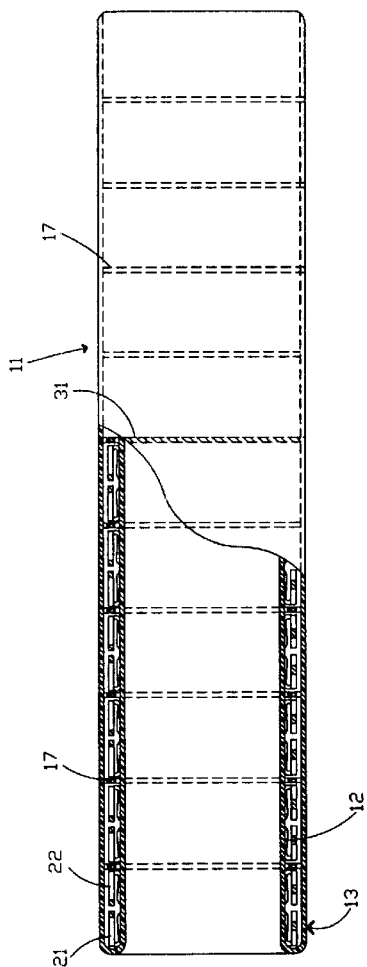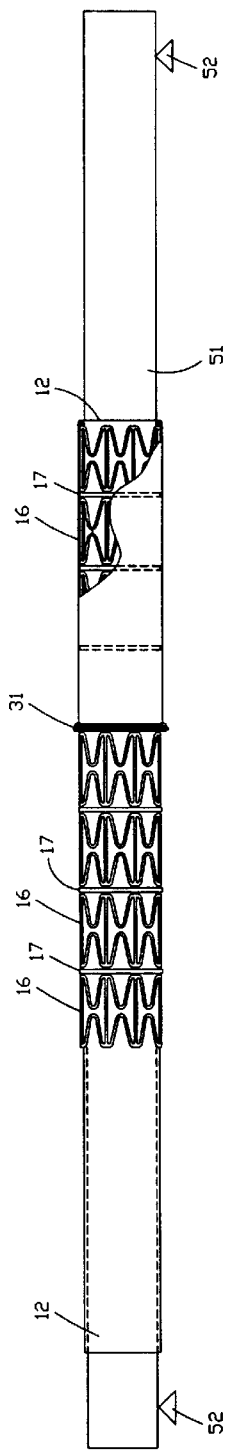

STENT GRAFT AND METHOD

This invention relates to a stent graft and method and more particularly to a covered flexible stent graft and method for making the same.

Stent grafts of various types have heretofore been provided. However, such stent grafts have not had the desired flexibility while retaining a consistent circumferential support. There is therefore a need for a new and improved stent graft and method for making the same.

In general, it is an object of the present invention to provide a stent graft and method in which a stent graft is provided which is very flexible.

Another object of the invention is to provide a stent graft of the above character which utilizes a minimum number of materials and elements which are exposed to blood and tissue.

Another object of the invention is to provide a stent graft and method of the above character which makes it possible to maintain a substantially constant length during expansion of the stent graft.

Another object of the invention is to provide a stent graft and method of the above character which can be used to locally deliver drugs or agents to improve the vascular benefit and long-term performance of the stent graft.

Another object of the invention is to provide a stent graft and method of the above character in which the stent graft can be economically manufactured.

Additional objects and features of the invention will appear from the following description in which the preferred embodiments are set forth in detail in conjunction with the accompanying drawings.

FIG. 1 is a partial isometric view of a stent graft incorporating the present invention FIG. 2 is an enlarged side elevational view of the stent graft shown in FIG. 1 with certain portions being broken away.

FIG. 3 is a side elevational view of the stent graft showing its method of manufacture.

FIG. 4 is a partial cross-sectional view showing another embodiment of the stent graft of the present invention.

Figure 5:
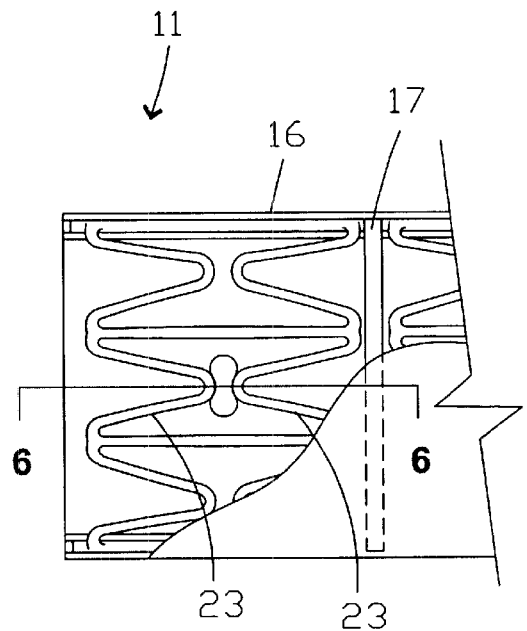
FIG. 5 is a partial side elevational view of a stent graft incorporating the present invention with certain portions broken away which includes the capabilities for delivering drugs and/or agents.

In general, the stent graft of the present invention is for implantation in a vessel in a human body and comprises inner and outer coaxial tubular sleeves formed of a flexible material compatible for use in the human body and each having first and second ends. A plurality of separate expandable metallic rings are axially disposed along the length of the inner and outer sleeves between the inner and outer sleeves. Each ring is comprised of first and second substantially circular elements having convolutions therein defining outer margins of the ring and a plurality of circumferentially spaced-apart struts extending between said substantially circular elements and being joined therewith to maintain a predetermined axial spacing between the substantially circular elements whereby on expansion of the rings, the length of the rings and the length of the stent graft are maintained. Bands of a flexible material compatible with the material of the inner and outer sleeves are disposed between the rings and within and between the inner and outer sleeves.

More in particular, the stent graft 11 of the present invention as shown in FIGS. 1 and 2 has a multilayer construction which is comprised essentially of three layers in which an inner sleeve 12 serves as one layer and an outer sleeve 13 serves as another layer and a plurality of juxtaposed rings 16 and bands 17 form an intermediate or third layer. The inner and outer sleeves 12 and 13 are preferably formed of the same material. However, if desired they can be formed of different materials. The material used for the sleeves 12 and 13 should be flexible and stretchable, i.e. capable of expanding. The material should be suitable for implantation in a vessel in a human body and typically may be a polymer. The material should be compatible with tissue and blood of the human body. One polymer found to be particularly satisfactory is expanded PTFE commonly called ePTFE. The ePTFE is desirable because it is a material which has pores that can enhance cell growth when implanted in a vessel in the human body. In addition, the ePTFE is very soft and can be readily expanded from a delivery unexpanded mode to an expanded mode as hereinafter described.

It is desirable that the wall thickness of the material utilized for the inner and outer sleeves be quite thin as for example ranging from 0.001" to 0.008" and preferably from 0.002" to 0.003". In connection with the selection of wall thickness it should be appreciated that during expansion of the stent graft 11 as hereinafter described, the wall thickness will decrease. The pore sizes can range from 10 $\mu$m to 90 $\mu$m and preferably between 20 to 60 $\mu$m. Pore size can be selected to optimize desired biological responses.

The rings 16 are formed of a suitable material such as stainless steel, titanium or tantalum with the latter material being particularly useful where optimum radiopacity is desired. The rings 16 are typically formed from a tubular material which is laser cut to provide the desired geometry as for example the geometry which is shown in FIGS. 1 and 2 of the drawings. Thus each ring 16 consists of first and second substantially circular elements 21 and 22 which have convolutions 23 therein generally in the form of a sine wave in which the maximums of each sine wave of the elements 21 and 22 are disposed opposite each other and are joined together and maintained in a predetermined spaced-apart relationship by struts 26 which typically are elongate and straight. As hereinafter explained, the struts 26 serve to maintain the length of the rings 16 in a axial direction as the rings are expanded. The wall thickness of the material utilized for forming the rings 16 can have a thickness ranging from 0.002" to 0.004" which after laser cutting are polished internally and externally with the axial lengths of the rings ranging from 2–3 mm. In order to reduce spacing between the circular elements 21 and 22 after expansion of the elements 21 and 22, a minimum of one element can be positioned so that it is opposite the maximum of another element.

The bands 17 are preferably formed of FEP (fluorinated ethylene polypropylene) because this material is very compatible with the ePTFE material utilized for the inner and outer sleeves 12 and 13. It is a particularly desirable material because it bonds very well to ePTFE when subjected to heat. Alternatively the bands 17 can be formed of PTFE which can be bonded to the sleeves by suitable means such as an adhesive or ultrasonic welding. It is desirable that the bands 17 be formed of a material which can fuse to the inner and outer sleeves 12 and 13.

The bands 17 typically preferably have the same wall thickness as the thickness of the material utilized for the rings 16. These bands 17 can have an axial length of 0.010"

0.050" with a preferable length ranging from 0.010" to 0.020". The bands 17 can have a wall thickness ranging from 0.001" to 0.004" to correspond to the thickness of the rings 16.

As can be seen from FIGS. 1 and 2, the rings 16 and the bands 17 are juxtaposed with respect to each other in alternating positions extending axially between the inner and outer sleeves 12 and 13. The inner and outer sleeves 12 and 13 can be bonded together by the use of the flexible bands 17 by applying heat to the outer sleeve 13 at appropriate circumferential locations. Alternatively, the entire multi-layer assembly can be placed in an oven at a suitable temperature ranging from 400 to 450° F. for a suitable period of time as for example 3 to 5 minutes to cause bonding of the bands 17 to the inner surface of the outer sleeve 13 and the outer surface of the inner sleeve 12.

By way of example, manufacture of the stent graft of the present invention can be accomplished by the method which is shown in FIG. 3 in which a cylindrical mandrel 51 is provided carried by supports 52 at opposite ends thereof. The mandrel 51 is formed of a suitable material such as stainless steel and is sized so that its outside diameter corresponds generally to the desired inside diameter of the inner sleeve 12.

In connection with the manufacture of the stent graft 11, it may be desirable prior to assembly to coat the surfaces of the inner sleeve 12 and the outer sleeve 13 which are to be in contact with blood and tissue of the human body with an appropriate bioactive/biocompatible coating such as that described in co-pending application Ser. No. 09/385,692 filed Aug. 30, 1999 now U.S. Pat. No. 6,159,531. In the manufacture of the stent graft of the present invention as shown in FIG. 3, the tubing which is to be utilized for the inner sleeve 12 can be everted so that the inner surface is facing outwardly and coated after which the tubing can be returned to its initial state by reversing the folding of the sleeve material of the tubing. This tubing material can then be utilized for the inner sleeve 12 having an inner surface which is coated. By selecting an inner sleeve 12 which extends beyond the end of the stent approximately one-half the length of the stent graft from opposite ends of the stent graft, a stent graft 11 can be provided which has coated inner and outer surfaces.

As shown in FIG. 3, a sleeve 12 which has its inside surface coated as hereinbefore described is placed over the mandrel 51 so that the ends of the sleeve extend beyond the mandrel 51 as shown in FIG. 3. As soon as this has been accomplished, the rings 16 and bands 17 can be placed sequentially over the inner sleeve 12 in appropriate positions on the sleeve so that the intermediate portion of the sleeve is covered by the rings 16 and bands 17 and with equal lengths of the sleeve extending beyond the intermediate portion. Thereafter, one end of the sleeve 12 as for example the right hand end as shown FIG. 3 can be everted and folded over one-half of the juxtaposed rings 16 and bands 17 to form a rounded end as shown on the left hand side of FIG. 2 to thereby encapsulate the rings 16 and bands 17 and to thereby provide an inner sleeve 12 and an outer sleeve 13. In a similar manner the left hand side can be everted and folded over to enclose the remaining rings 16 and bands 17 to form another closed end to provide the inner sleeve 12 and the outer sleeve 13 and to form a seam 31 between the two half portions of the inner sleeve 12 forming the outer sleeve 13. Thus the two ends of the half portions of the outer sleeve 13 can be bonded together by suitable means such as by the use of heat. As soon as this has been accomplished, the completed stent graft can be removed from the mandrel 51 and another stent graft fabricated in a similar manner.

Alternatively if desired, the inner sleeve 12 and the outer sleeve 13 can be formed of separate parts with the inner surface of the inner sleeve 12 being coated and with the outer surface of the outer sleeve 13 being coated. With the use of such separate inner and outer sleeves 12 and 13, the inner sleeve 12 can be inserted onto the mandrel 51 and thereafter the rings 16 and bands 17 can be sequentially positioned thereon throughout the length of the inner sleeve. Thereafter the outer sleeve 13 can be slid over the rings 16 and bands 17 to cover the same. After this has been accomplished, the inner and outer sleeves 12 and 13 can be cut into appropriate lengths by cutting adjacent a band 17 so that the inner space between the sleeves 12 and 13 will be sealed as shown in FIG. 4.

In either of the methods utilized for manufacture of the stent graft shown in FIGS. 3 and 4 it may be desirable to provide radiopaque markers at opposite ends of the stent graft to facilitate its placement in a vessel as hereinafter described. This can be readily accomplished by selecting rings 16 at opposite ends of the stent graft which are formed of a more radiopaque material as for example titanium or tantalum whereas intermediate rings can be formed of a less expensive material such a stainless steel.

In connection with the stent graft of the present invention, it has been found that it may be desirable to utilize the stent graft to locally deliver different drugs or agents into the vessel into which the stent graft is to be implanted to improve the vascular benefit and long term performance of the stent graft. Types of drugs or agents that may prove beneficial include substances that reduce the thrombogenic, inflammatory or smooth muscle cell proliferative response of the vessel to the stent graft. Specific examples of such drugs or agents may include heparin, phosphorylcholine, albumin, dexamethasone, paelitaxel and vascular endothelial growth factor (VEGF).

Figure 6:
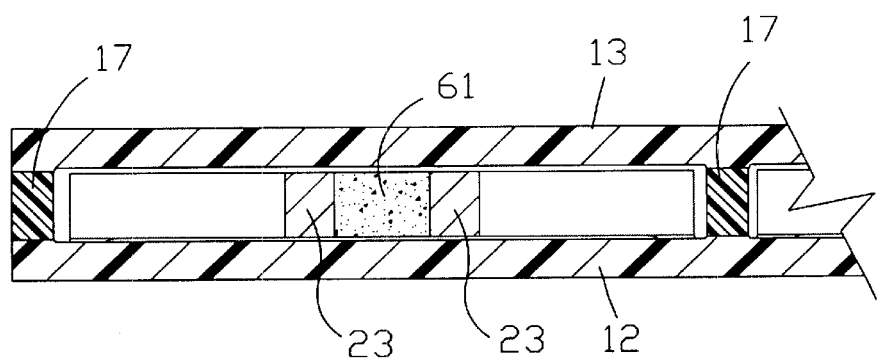
FIG. 6 is an enlarged cross-sectional view taken along the line 6—6 of FIG. 5.

The drug or agents can be incorporated into the stent graft in various ways. For example the drug or agent can be injected in the form of a gel or powder into spaces or pockets provided by the rings 16 between the elements 21, 22 and the struts 26 which are encapsulated between the inner and outer sleeves 12 and 13. Alternatively the stent graft 11 can be coated with a drug loaded polymer matrix which dissolves in the body fluids after implantation into the vessel. Alternatively, the drug or agent can be supplied in a powder which has been formed into a solid tablet 61 positioned between the convolutions 23 as shown in FIGS. 5 and 6. Such tablets would gradually dissolve after implantation because of the porous nature of the inner and outer sleeves 12 and 13 formed of ePTFE.

Figure 7:
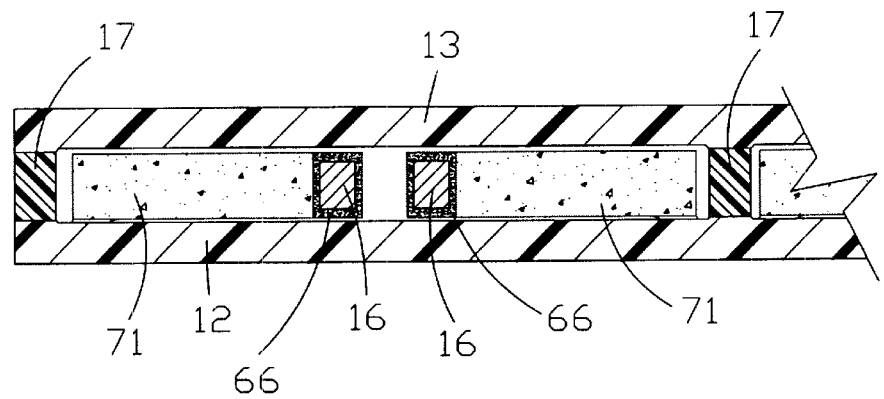
FIG. 7 is a partial cross-sectional view of another embodiment of a stent graft incorporating the present invention having drug or agent delivery capabilities.

Another embodiment of the stent graft incorporating the present invention is shown in FIG. 7 in which the drug is delivered by a drug loaded coating 66 provided on the stent 16. Such a coating would release its drug carried thereby upon implantation of the stent graft in the vessel of the patient. In addition as shown in FIG. 7, a dissolvable polymer 71 can be provided in the interstices between the convolutions 23 of the rings 16. As an alternative, the stent graft can be soaked in a solvent with a drug after assembly with the solvent being flashed off to leave the drug disposed in the interstices of the material utilized for forming the inner and outer sleeves 12 and 13.

The drugs delivered in the manner described above can introduce the drugs or agents in a delivery matrix which dissolves in a liquid environment. Alternatively the drug or agent can be delivered in a delivery matrix which liquefies at an elevated ("body") temperature. Also it should be appreciated that a dilatation balloon which typically is used for delivering a stent graft of the type hereinbefore described can be utilized for forcing a drug or agent out of pockets formed between the inner and outer sleeves during delivery of the stent graft into the vessel.

After the stent graft has been manufactured in the manner hereinbefore described it can be crimped onto the balloon of a balloon delivery catheter and delivered into a vessel in a conventional manner as for example through the femoral artery of a patient to a vessel within the body of the patient as for example an arterial vessel in the wall of the heart. The movement of the stent graft 11 can be readily observed by observing the radiopaque rings carried by the extremities of the stent graft. When it is properly positioned, the balloon can be inflated to expand the stent graft 11 into the desired location. The rings 16 and the bands 17 in the inner and outer sleeves 12 and 13 readily accommodate the desired expansion to a suitable size as for example from 2–5 mils. This expansion of the stent graft can be accommodated without changing the length of the stent graft because the struts 26 maintain the axial lengths of the rings and thereby maintain the axial length of the stent raft 11. The rings 16 provide the desired circumferential rigidity and serve to maintain the stent graft in the expanded position. Since there is no metal interconnecting the rings 16, the flexible bands 17 disposed between the rings serve to provide flexibility in the stent graft so that the stent graft can readily accommodate any bends in the vessel during and after deployment. For this reason, the stent graft can be readily positioned in the desired location.

When the stent graft which has been positioned in the vessel has been manufactured and assembled to incorporate drug or agent delivery capabilities as hereinbefore described, the drug or agent which has been incorporated therein is locally delivered from the stent graft to provide the desired results as for example to provide vascular benefits and enhance the long term performance of the stent graft.

The stent graft and method of the present invention have many advantages. There has been provided a stent graft which is physiologically compatible and highly flexible and is comprised of a minimum number of materials and elements which are exposed to blood and tissue in the human body. Because of the construction, the metal which is used for the rings is completely encapsulated within the inner and outer sleeves. Thus only one material as for example the ePTFE which is utilized for the inner and outer sleeves is introduced into the vessel. In utilizing coatings for the stent graft for various purposes as for example inhibiting clotting, enhancing endothelial growth, etc., these can be accomplished by a single coating process because only one material need be coated. In contrast to a situation where both metal and a polymer are exposed to the blood and tissue, both must be coated in separate processes. The desired radiopacity at the extremities of the stent graft can be readily achieved because since the rings are modular components of the stent graft, only one or possibly two need be made of the more expensive radiopaque material. By the elimination of connecting metal between the metallic rings, the flexibility of the stent graft is greatly increased. The flexible bands provided between the rings provide circumferential support between the rings. They also serve as circumferential lines of attachment between the inner and outer sleeves and also provide for support of the spaces between the rings. The construction utilized for the stent graft is one which lends itself to ease of manufacture and less labor intensive manufacture. The construction utilized also lends itself for delivery of drugs or agents to improve the vascular benefit and long term performance of the stent graft.

What is claimed:

1. A stent graft for implantation in a vessel in a human body comprising inner and outer coaxial tubular sleeves formed of a flexible material compatible for use in the human body and each having first and second ends, a plurality of separate expandable metallic rings disposed axially within and between the inner and outer sleeves and separate bands of a flexible material compatible with the flexible material utilized for the inner and outer sleeves disposed between the rings and within and between the inner and outer sleeves.

2. A stent graft as in claim 1 wherein each ring is comprised of first and second substantially circular elements having convolutions therein defining the outer margins of the ring and a plurality of circumferentially spaced-apart struts extending between said substantially circular elements and being joined therewith to maintain a predetermined axial spacing between the substantially circular elements so that the length of the ring is maintained during expansion of the ring.

3. A stent graft as in claim 1 wherein said convolutions are generally sinusoidal having maximums and minimums, the maximum of one element being disposed opposite the maximum of the other element with the spaced-apart struts extending between the maximums.

4. A stent graft as in claim 1 wherein said flexible material for the inner and outer tubular sleeves is an ePTFE.

5. A stent graft as in claim 4 wherein said bands are formed of FEP.

6. A stent graft as in claim 1 wherein the bands are bonded to the outer surface of the inner sleeve and to the inner surface of the outer sleeve.

7. A stent graft as in claim 1 wherein at least one of the rings at one of the ends of the stent graft is formed of a radiopaque material with the other rings being formed of a less radiopaque material.

8. A stent graft as in claim 1 wherein the rings on opposite ends of the stent graft are formed of a radiopaque material.

9. A stent graft as in claim 1 further including a biologically active coating carried by the inner surface of the inner sleeve and the outer surface of the outer sleeve.

10. A stent graft as in claim 1 further including means carried by the stent graft for providing local delivery of drugs or agents into the vessel after the stent graft has been positioned in the vessel.

11. A stent graft as in claim 10 wherein the drug or agent is disposed in pockets formed in the rings and between the inner and outer sleeves.

12. A stent graft as in claim 10 where the drug or agent is in a solid tablet form.

13. A stent graft as in claim 10 wherein the drug or agent is carried by a coating provided on the rings.

14. A stent graft as in claim 10 wherein said drug or agent is in liquid form.

15. A stent graft as in claim 10 wherein said drug or agent is in powder form.

16. A method for manufacturing a stent graft for implantation in a vessel in a human body by the use of a sleeve of a flexible material compatible for use in a human body, separate expandable metallic rings and separate expandable bands formed of a flexible material and by the use of a mandrel having an outside diameter corresponding to the inside diameter of the inner sleeve comprising placing the inner sleeve over the mandrel, placing the rings and bands on the inner sleeve extending axially of the sleeve so that the rings and bands are substantially juxtaposed and are alternating with respect to each other axially of the sleeve and introducing an outer sleeve over the juxtaposed rings and bands and bonding the bands to the inner and outer sleeves.

17. A method as in claim 16 wherein the outer sleeve is formed by everting lengths of the inner sleeve extending from opposite ends to extend over the rings and bands to cover the rings and bands.

18. A method as in claim 16 further including the step of coating the outer surface of the outer sleeve and the inner surface of the inner sleeve with a biologically active coating.

19. A method as in claim 16 further including the step of sealing the ends of the inner and outer sleeves so that the rings and bands are encapsulated therein.

20. A method as in claim 16 further including the step of coating the inner surface of the inner sleeve prior to its placement on the mandrel.

* * * * *